US010341782B2

(12) United States Patent
Kitchens, II et al.

(10) Patent No.: US 10,341,782 B2
(45) Date of Patent: Jul. 2, 2019

(54) ULTRASONIC RECEIVER WITH COATED PIEZOELECTRIC LAYER

(71) Applicant: QUALCOMM Incorporated, San Diego, CA (US)

(72) Inventors: Jack Conway Kitchens, II, Town of Tonawanda, NY (US); John Keith Schneider, Williamsville, NY (US); Stephen Michael Gojevic, Lockport, NY (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 15/925,636

(22) Filed: Mar. 19, 2018

(65) Prior Publication Data
US 2018/0213333 A1 Jul. 26, 2018

Related U.S. Application Data

(62) Division of application No. 14/175,876, filed on Feb. 7, 2014, now abandoned.
(Continued)

(51) Int. Cl.
*H04R 17/00* (2006.01)
*A61B 5/1172* (2016.01)
(Continued)

(52) U.S. Cl.
CPC .......... *H04R 17/005* (2013.01); *A61B 5/1172* (2013.01); *B06B 1/0688* (2013.01);
(Continued)

(58) Field of Classification Search
USPC ...................................... 367/137
See application file for complete search history.

(56) References Cited

U.S. PATENT DOCUMENTS 5,133,037 A * 7/1992 Yoon ....................... G02F 1/065
                                                    359/332
5,670,871 A * 9/1997 Man ........................ G01R 1/071
                                                    324/754.06
(Continued)

FOREIGN PATENT DOCUMENTS

CN       101315823 A      12/2008
CN       101533170 A       9/2009
(Continued)

OTHER PUBLICATIONS

International Search Report and Written Opinion—PCT/US2014/039985—ISA/EPO—dated Nov. 20, 2014.
(Continued)

*Primary Examiner* — James R Hulka
(74) *Attorney, Agent, or Firm* — Weaver Austin Villeneuve & Sampson LLP

(57) ABSTRACT

This disclosure provides systems, methods and apparatus related to an ultrasonic receiver for detecting ultrasonic energy received at a first surface of the ultrasonic receiver. The ultrasonic receiver includes an array of pixel circuits disposed on a substrate, each pixel circuit in the array including at least one thin film transistor (TFT) element and having a pixel input electrode electrically coupled to the pixel circuit. The ultrasonic receiver is fabricated by forming a piezoelectric layer so as to be in electrical contact with the pixel input electrodes. Forming the piezoelectric layer includes coating a solution containing a polymer onto the array of pixel circuits, crystallizing the polymer to form a crystallized polymer layer and poling the crystallized polymer layer.

12 Claims, 10 Drawing Sheets

Related U.S. Application Data

(60) Provisional application No. 61/830,572, filed on Jun. 3, 2013.

(51) Int. Cl.
  *B06B 1/06* (2006.01)
  *G06K 9/00* (2006.01)
  *G01H 1/00* (2006.01)
  *G01H 11/08* (2006.01)

(52) U.S. Cl.
  CPC ............... *G01H 1/00* (2013.01); *G01H 11/08* (2013.01); *G06K 9/0002* (2013.01)

(56) References Cited

U.S. PATENT DOCUMENTS

| | | | |
|---|---|---|---|
| 7,223,243 B2 | 5/2007 | Morris et al. | |
| 7,400,750 B2 | 7/2008 | Nam | |
| 7,616,786 B2 | 11/2009 | Setlak | |
| 7,955,641 B2 | 6/2011 | Schneider et al. | |
| 8,139,827 B2 | 3/2012 | Schneider et al. | |
| 8,183,745 B2 | 5/2012 | Trolier-McKinstry et al. | |
| 8,193,685 B2 | 6/2012 | Klee et al. | |
| 8,201,739 B2 | 6/2012 | Schneider et al. | |
| 8,247,802 B2 | 8/2012 | Nomura et al. | |
| 8,288,776 B2 | 10/2012 | Choi et al. | |
| 8,724,832 B2 | 5/2014 | Stephanou et al. | |
| 9,157,821 B2 | 10/2015 | Robert et al. | |
| 9,170,668 B2 | 10/2015 | Schneider et al. | |
| 9,262,003 B2 | 2/2016 | Kitchens et al. | |
| 2004/0263483 A1* | 12/2004 | Aufderheide ....... G06F 3/03545 345/173 | |
| 2006/0286311 A1 | 12/2006 | Okazaki et al. | |
| 2007/0029899 A1 | 2/2007 | Matsuzawa | |
| 2007/0089525 A1 | 4/2007 | Momose et al. | |
| 2007/0231462 A1 | 10/2007 | Araki et al. | |
| 2007/0258628 A1 | 11/2007 | Schneider et al. | |
| 2008/0018199 A1* | 1/2008 | Trolier-McKinstry ..................... B06B 1/0629 310/311 | |
| 2008/0033298 A1 | 2/2008 | Habu et al. | |
| 2008/0231145 A1 | 9/2008 | Nagano et al. | |
| 2009/0047445 A1* | 2/2009 | Schneider ............... H01L 41/45 427/562 | |
| 2010/0052478 A1 | 3/2010 | Schneider et al. | |
| 2010/0277040 A1* | 11/2010 | Klee ..................... B06B 1/0292 310/324 | |
| 2010/0328328 A1* | 12/2010 | Choi ..................... B06B 1/0688 345/530 | |
| 2011/0034912 A1 | 2/2011 | De Graff et al. | |
| 2012/0111119 A1 | 5/2012 | Small et al. | |
| 2012/0144920 A1 | 6/2012 | Wong et al. | |
| 2013/0051587 A1* | 2/2013 | Stephanou ............. G01H 11/08 381/190 | |
| 2014/0035935 A1 | 2/2014 | Shenoy et al. | |
| 2014/0198072 A1 | 7/2014 | Schuele et al. | |
| 2014/0218802 A1 | 8/2014 | Saito et al. | |
| 2014/0352440 A1 | 12/2014 | Fennell et al. | |
| 2014/0354596 A1 | 12/2014 | Djordjev et al. | |
| 2014/0354597 A1 | 12/2014 | Kitchens, II et al. | |
| 2014/0354905 A1 | 12/2014 | Kitchens et al. | |
| 2014/0355387 A1 | 12/2014 | Kitchens, II et al. | |
| 2014/0359757 A1 | 12/2014 | Sezan et al. | |
| 2015/0123931 A1* | 5/2015 | Kitchens ............... G06F 3/0414 345/174 | |
| 2015/0241393 A1 | 8/2015 | Ganti et al. | |
| 2015/0286318 A1 | 10/2015 | Morein et al. | |
| 2016/0026842 A1 | 1/2016 | Withers et al. | |
| 2016/0107194 A1 | 4/2016 | Panchawagh et al. | |
| 2016/0171276 A1 | 6/2016 | Chiang et al. | |
| 2016/0210496 A1 | 7/2016 | Lin et al. | |
| 2017/0317269 A1* | 11/2017 | Zhang ................... H01L 41/047 | |
| 2017/0364726 A1 | 12/2017 | Buchan et al. | |

FOREIGN PATENT DOCUMENTS

| | | | |
|---|---|---|---|
| CN | 101691202 A | 4/2010 | |
| CN | 102596044 A | 7/2012 | |
| DE | 19833928 A1 | 2/2000 | |
| JP | S58186981 A | 11/1983 | |
| JP | 2012125560 A | 7/2012 | |
| JP | 2012127945 A | 7/2012 | |
| KR | 20010110247 A | 12/2001 | |
| KR | 100363279 B1 | 2/2003 | |
| KR | 20080109327 A | 12/2008 | |
| TW | 200625155 A | 7/2006 | |
| WO | WO-2008015917 A1 | 2/2008 | |
| WO | WO-2015105320 A1 | 7/2015 | |

OTHER PUBLICATIONS

International Written Opinion—PCT/US2014/039985—dated Jun. 8, 2015.
U.S. Office Action dated Aug. 4, 2016 issued in U.S. Appl. No. 14/175,876.
U.S. Final Office Action dated Jan. 5, 2017 issued in U.S. Appl. No. 14/175,876.
U.S. Office Action dated Sep. 26, 2017 issued in U.S. Appl. No. 14/175,876.
Lee J.S., et al., "Surface Functionalization of a Poly(vinylidene fluoride): Effect on the Adhesive and Piezoelectric Properties", ACS Applied Materials & Interfaces, 2009, vol. 1 (12), pp. 2902-2908.
Pangracious V., et al., "Three-Dimensional Integration: A More Than Moore Technology", In: Three-Dimensional Design Methodologies for Tree-based FPGA-Architecture, Jan. 1, 2015, vol. 350, Springer, XP055405152, ISSN: 1876-1100, ISBN: 978-3-642-05166-1, DOI: 10.1007/978-3-319-19174-4_2, pp. 13-41.
Partial International Search Report—PCT/US2014/039985—ISA/EPO—dated Sep. 17, 2014.
Pecora A., et al., "Flexible PVDF-TrFE pyroelectric Sensor Driven by Polysilicon Thin Film Transistor Fabricated on Ultra-Thin Polyimide Substrate", Sensors and Actuators A: Physical, 2012, vol. 185, pp. 39-43.
Serrado Nunes. J., et al., "Electrical and Microstructural Changes of P-PVDF under Different Processing Conditions by Scanning Force Microscopy," Materials Research Society Symposium Proceedings, 2007, vol. 949, pp. 1-6.
Taiwan Search Report—TW103119261—TIPO—dated Oct. 23, 2017.
Wang Z., "3-D Integration and Through-Silicon Vias in MEMS and Microsensors", Journal of Microelectromechanical Systems, Oct. 1, 2015, vol. 24, No. 5, XP055405155, ISSN: 1957-7157, DOI: 10.1109/JMEMS.2015.2448681, pp. 1211-1244.
Xu H., et al., "Domain Stabilization Effect of Interlayer on Ferroelectric Poly(Vinylidene Fluoride-Trifluoroethylene) Copolymer Ultrathin Film," Journal of Applied Physics, 2009, vol. 105 (3), pp. 34107-1-34107-6.
Kressmann R., et al, "New Results of Micromachined Silicon Subminiature Microphones using Piezoelectric Polymer Layers", Proceedings 9th International Symposium on Electrets (ISE 9), 1996, pp. 1044-1049.

* cited by examiner

ULTRASONIC RECEIVER WITH COATED PIEZOELECTRIC LAYER

CROSS-REFERENCE TO RELATED APPLICATIONS

This application is a divisional of U.S. patent application Ser. No. 14/175,876, filed on Feb. 7, 2014 and claims priority under 35 U.S.C. § 119 to U.S. Provisional Patent Application No. 61/830,572, filed Jun. 3, 2013, entitled "ULTRASONIC RECEIVER WITH COATED PIEZO-ELECTRIC LAYER," and assigned to the assignee hereof. The disclosures of the prior applications are considered part of, and are incorporated by reference in, this disclosure for all purposes.

TECHNICAL FIELD

This disclosure relates generally to an ultrasonic receiver.

DESCRIPTION OF THE RELATED TECHNOLOGY

In an ultrasonic sensor system, an ultrasonic transmitter may be used to send an ultrasonic wave through an ultrasonically transmissive medium or media and towards an object to be detected. The transmitter may be operatively coupled with an ultrasonic sensor configured to detect portions of the ultrasonic wave that are reflected from the object. For example, in ultrasonic fingerprint imagers, an ultrasonic pulse may be produced by starting and stopping the transmitter during a very short interval of time. At each material interface encountered by the ultrasonic pulse, a portion of the ultrasonic pulse is reflected.

For example, in the context of an ultrasonic fingerprint imager, the ultrasonic wave may travel through a platen on which a person's finger may be placed to obtain a fingerprint image. After passing through the platen, some portions of the ultrasonic wave encounter skin that is in contact with the platen, e.g., fingerprint ridges, while other portions of the ultrasonic wave encounter air, e.g., valleys between adjacent ridges of a fingerprint, and may be reflected with different intensities back towards the ultrasonic sensor. The reflected signals associated with the finger may be processed and converted to a digital value representing the signal strength of the reflected signal. When multiple such reflected signals are collected over a distributed area, the digital values of such signals may be used to produce a graphical display of the signal strength over the distributed area, for example by converting the digital values to an image, thereby producing an image of the fingerprint. Thus, an ultrasonic sensor system may be used as a fingerprint imager or other type of biometric scanner. In some implementations, the detected signal strength may be mapped into a contour map of the finger that is representative of the depth of the ridge structure detail.

SUMMARY

The systems, methods and devices of the disclosure each have several innovative aspects, no single one of which is solely responsible for the desirable attributes disclosed herein.

One innovative aspect of the subject matter described in this disclosure can be implemented in an apparatus that includes an ultrasonic receiver for detecting ultrasonic energy received at a first surface of the ultrasonic receiver. The ultrasonic receiver includes an array of pixel circuits disposed on a substrate, each pixel circuit in the array including at least one thin film transistor (TFT) element and having a pixel input electrode electrically coupled to the pixel circuit. The ultrasonic receiver is fabricated by forming a piezoelectric layer so as to be in electrical contact with the pixel input electrodes. Forming the piezoelectric layer includes coating a solution containing a polymer onto the array of pixel circuits, crystallizing the polymer to form a crystallized polymer layer and poling the crystallized polymer layer.

In an implementation, the pixel input electrode may be formed from a conductive film.

In another implementation, forming the piezoelectric layer may include coating an adhesion promoter onto the array of pixel circuits.

In a further implementation, coating the solution containing the polymer may be performed by spin coating, slot coating, dipping, dispensing, spraying, or another coating process.

In yet another implementation, the polymer may include a ferroelectric polymer. The polymer may have a characteristic Curie temperature and a melting point, and crystallizing the polymer may include baking the polymer at a temperature between the Curie temperature and the melting point for at least one hour.

In another implementation, a conductive material may be applied to electrically short terminals of the pixel circuits to ground prior to the poling. The conductive material may be a conductive rubber or a conductive ink.

In a further implementation, the apparatus may include a receiver bias electrode deposited on the piezoelectric layer. The receiver bias electrode may include a first sublayer of copper and a second sublayer of nickel. The first sublayer may be about 150 angstroms thick and the second sublayer of nickel may be about 850 angstroms thick.

In an implementation, a method for fabricating an ultrasonic receiver configured to detect ultrasonic energy received at a first surface of the ultrasonic receiver includes forming a piezoelectric layer so as to be in electrical contact with pixel input electrodes, where the ultrasonic receiver includes an array of pixel circuits disposed on a substrate, each pixel circuit in the array including at least one thin film transistor (TFT) element and having a pixel input electrode electrically coupled to the pixel circuit. Forming the piezoelectric layer includes coating a solution containing a polymer onto the array of pixel circuits, crystallizing the polymer to form a crystallized polymer layer and poling the crystallized polymer layer. Poling may include applying an electric field with a field strength between 150 and 200 volts per micron through the polymer layer.

In an implementation, an apparatus includes an ultrasonic transmitter, a platen and an ultrasonic receiver disposed between the ultrasonic transmitter and the platen, the ultrasonic receiver including an array of pixel circuits disposed on a substrate, each pixel circuit in the array including a thin film transistor (TFT) element and having a pixel input electrode electrically coupled to the pixel circuit, the ultrasonic receiver being configured to detect ultrasonic energy reflected from an object in contact with the platen, the reflected ultrasonic energy resulting from interaction of ultrasonic energy emitted by the ultrasonic transmitter and the object, the ultrasonic receiver including a piezoelectric layer disposed between the array of pixel circuits and the platen. The piezoelectric layer is in electrical contact with the pixel input electrodes. The piezoelectric layer is formed by: coating a solution containing a polymer onto the array of pixel circuits, crystallizing the polymer to form a crystallized polymer layer, and poling the crystallized polymer coating.

In an implementation, an apparatus includes an ultrasonic receiver for detecting ultrasonic energy received at a first surface of the ultrasonic sensor. The ultrasonic sensor includes an array of pixel circuits disposed on a substrate, each pixel circuit in the array including at least one thin film transistor (TFT) element and having a pixel input electrode electrically coupled to the pixel circuit, and a piezoelectric layer in electrical contact with the pixel input electrodes. The piezoelectric layer includes a poled crystallized polymer layer.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

Like reference numbers and designations in the various drawings indicate like elements.

Like reference numbers and designations in the various drawings indicate like elements.

DETAILED DESCRIPTION

Figure 1A:
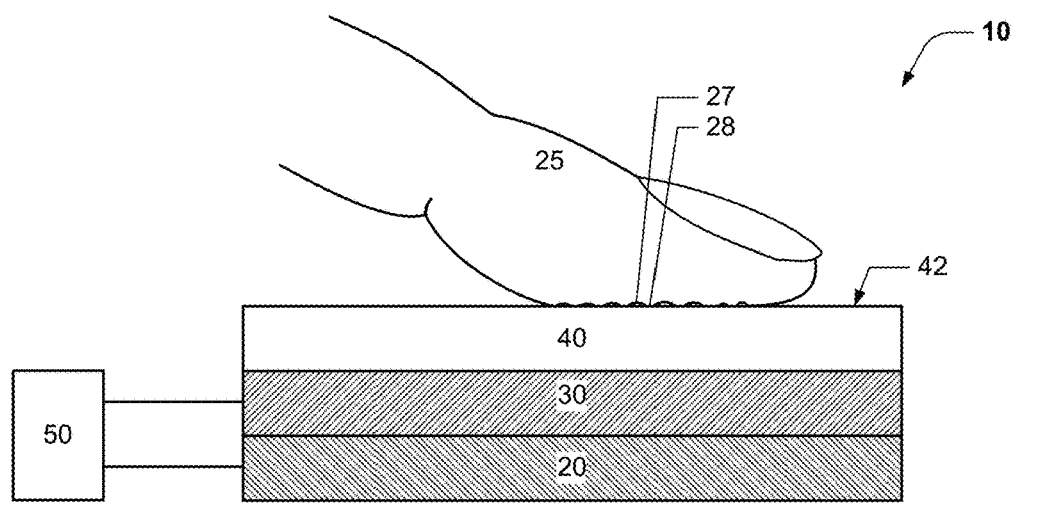
FIGS. 1A-1C show an example of a schematic diagram of an ultrasonic sensor system.

The following description is directed to certain implementations for the purposes of describing the innovative aspects of this disclosure. However, a person having ordinary skill in the art will readily recognize that the teachings herein can be applied in a multitude of different ways. The described implementations may be implemented in any device, apparatus, or system for ultrasonic sensing. In addition, it is contemplated that the described implementations may be included in or associated with a variety of electronic devices such as, but not limited to: mobile telephones, multimedia Internet enabled cellular telephones, mobile television receivers, wireless devices, smartphones, Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), computer monitors, auto displays (including odometer and speedometer displays, etc.), cockpit controls and/or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also can be used in applications such as, but not limited to, electronic switching devices, radio frequency filters, sensors, accelerometers, gyroscopes, motion-sensing devices, magnetometers, inertial components for consumer electronics, parts of consumer electronics products, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

Particular implementations of the subject matter described in this disclosure can be implemented to realize one or more of the following potential advantages. Compared to ultrasonic fingerprint sensors that have a focused transducer positioned by an electromechanical actuator motor to generate images, the presently disclosed techniques provide for a large-area fingerprint sensor that may be advantageously employed in mobile applications, for example. By avoiding an electromechanical actuator motor, the expense mass and volume of the fingerprint sensor may be reduced.

Instead, a thin film transistor (TFT) substrate having addressable sensing elements is coated with a piezoelectric film, to create an area array ultrasonic sensor. More particularly, a piezoelectric layer is formed so as to be in electrical contact with elements of the TFT substrate. Particular techniques are described for forming the piezoelectric layer so as to avoid damage to sensitive elements of the TFT substrate.

The implementations described herein relate to an ultrasonic sensor that includes an array of pixel circuits electrically connected or otherwise coupled to a piezoelectric layer. The piezoelectric layer may be formed by coating a solution containing a copolymer onto a first side of the array. The copolymer may be crystallized to form a crystallized copolymer layer. The crystallized copolymer layer may then be poled in order to create the piezoelectric layer. Advantageously, the piezoelectric layer is fabricated on, and disposed in direct electrical contact with, the array of pixel circuits. For example, where each pixel circuit includes one or more thin film transistor (TFT) elements, a pixel input electrode of the pixel circuit is electrically coupled to the piezoelectric layer.

Figure 1B:
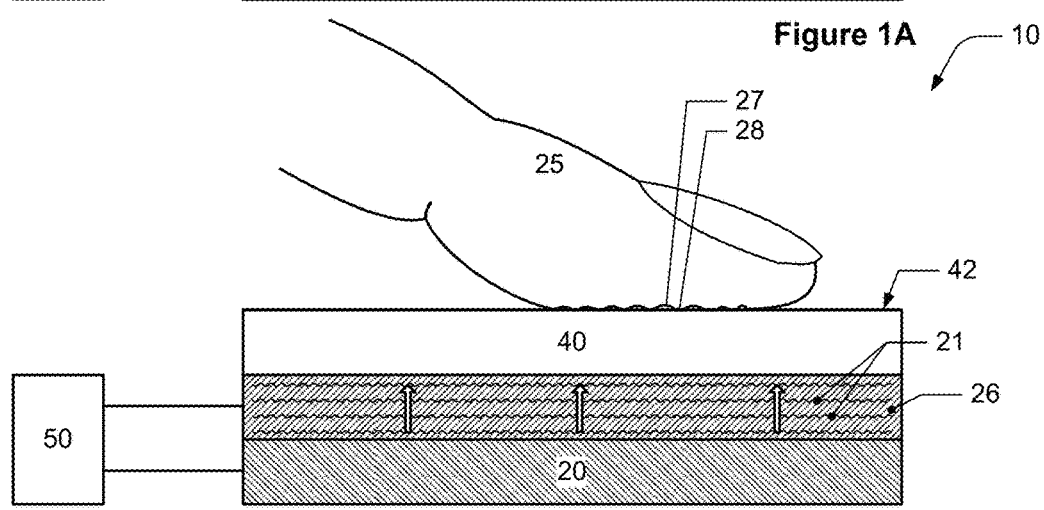
Figure 1C:
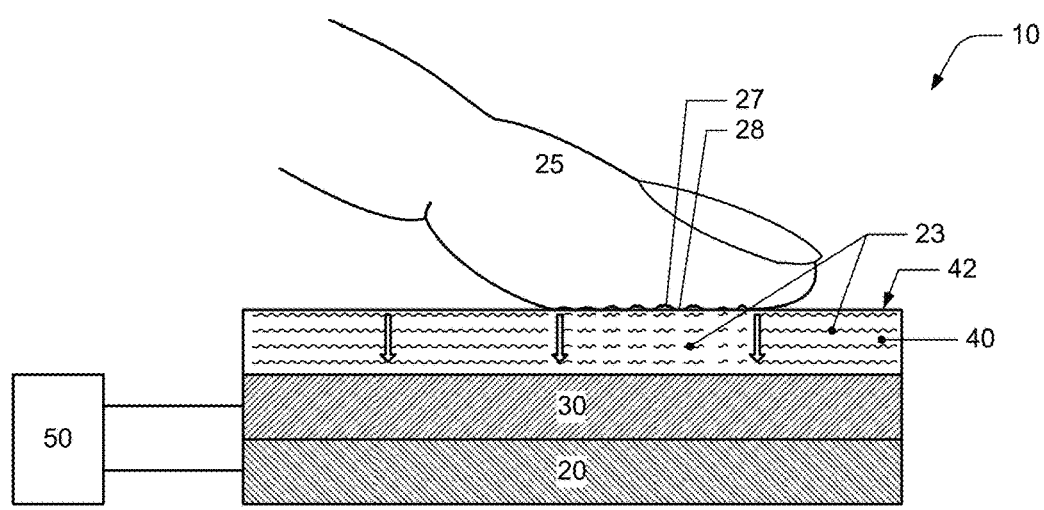

FIGS. 1A-1C show an example of a schematic diagram of an ultrasonic sensor system. As shown in FIG. 1A, ultrasonic sensor system 10 includes an ultrasonic transmitter 20 and an ultrasonic receiver 30 under a platen 40. The ultrasonic transmitter 20 may be a piezoelectric transmitter that can generate ultrasonic waves 21 (see FIG. 1B). The ultrasonic receiver 30 includes a piezoelectric material and an array of pixel circuits disposed on a substrate. In operation, the ultrasonic transmitter 20 generates an ultrasonic wave 21 that travels through the ultrasonic receiver 30 to the exposed surface 42 of the platen 40. At the exposed surface 42 of the platen 40, the ultrasonic energy may either be absorbed or scattered by an object 25 that is in contact with the platen 40, such as the skin of a fingerprint ridge 28, or reflected back. In those locations where air contacts the exposed surface 42 of the platen 40, e.g., valleys 27 between fingerprint ridges 28, most of the ultrasonic wave 21 will be reflected back toward the ultrasonic receiver 30 for detection (see FIG. 1C). Control electronics 50 may be coupled to the ultrasonic transmitter 20 and ultrasonic receiver 30 and may supply timing signals that cause the ultrasonic transmitter 20 to generate one or more ultrasonic waves 21. The control electronics 50 may then receive signals from the ultrasonic receiver 30 that are indicative of reflected ultrasonic energy 23. The control electronics 50 may use output signals received from the ultrasonic receiver 30 to construct a digital image of the object 25. In some implementations, the control electronics 50 may also, over time, successively sample the output signals to detect movement of the object 25.

Figure 2:
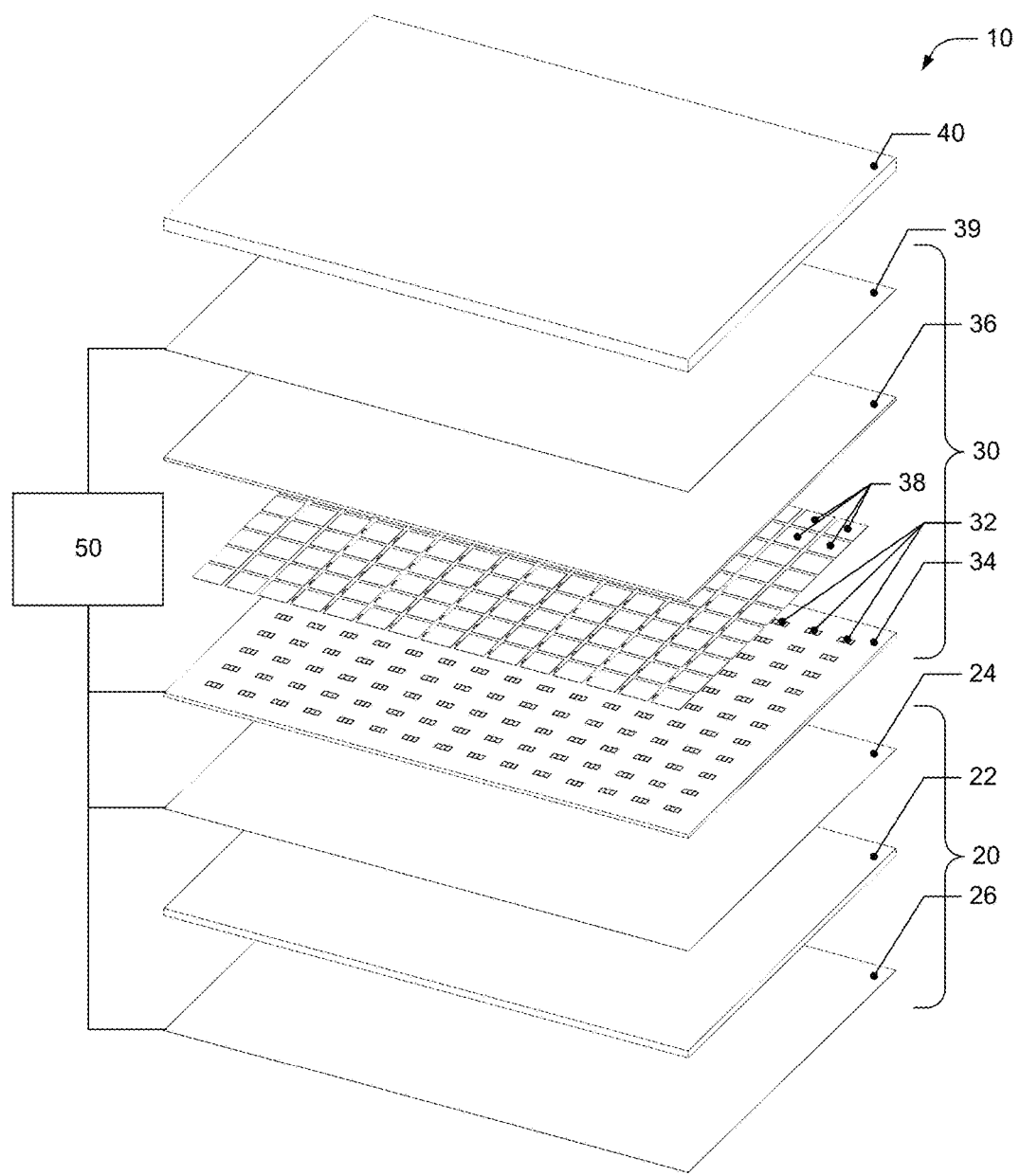
FIG. 2 shows an example of an exploded view of an ultrasonic sensor system.

FIG. 2 shows an example of an exploded view of an ultrasonic sensor system 10 including an ultrasonic transmitter 20 and an ultrasonic receiver 30 under a platen 40. The ultrasonic transmitter 20 may be a plane wave generator including a substantially planar piezoelectric transmitter layer 22. Ultrasonic waves may be generated by applying a voltage to the piezoelectric layer to expand or contract the layer, depending upon the signal applied, thereby generating a plane wave. The voltage may be applied to the piezoelectric transmitter layer 22 via a first transmitter electrode 24 and a second transmitter electrode 26. In this fashion, an ultrasonic wave may be made by changing the thickness of the layer. This ultrasonic wave travels toward a finger (or other object to be detected), passing through the platen 40. A portion of the wave not absorbed by the object to be detected may be reflected so as to pass back through the platen 40 and be received by the ultrasonic receiver 30. The first and second transmitter electrodes 24 and 26 may be metallized electrodes, for example, metal layers that coat opposing sides of the piezoelectric transmitter layer 22.

Figure 3A:
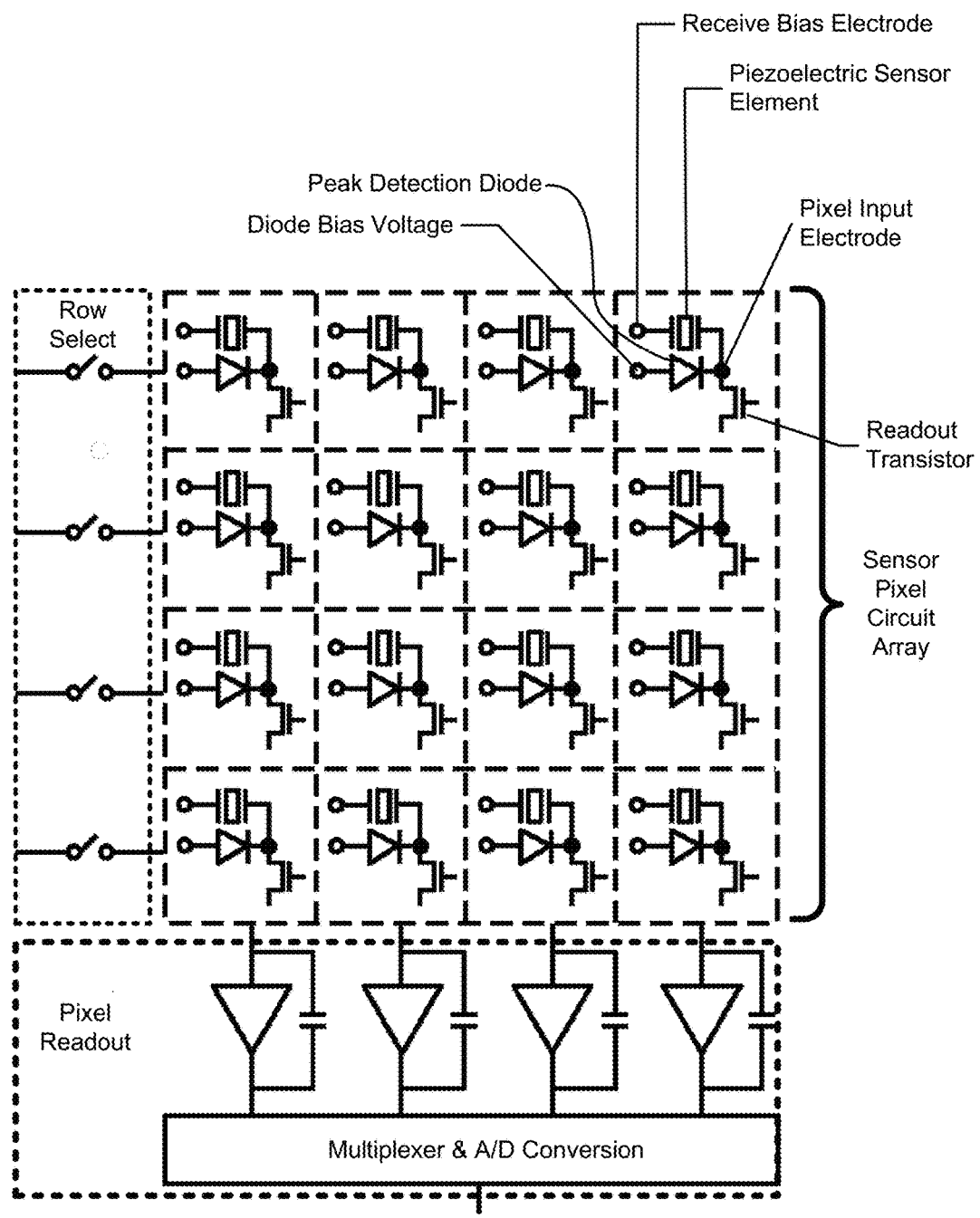
FIG. 3A shows an example of a 4×4 pixel array of pixels for an ultrasonic sensor.

The ultrasonic receiver 30 may include an array of pixel circuits 32 disposed on a substrate 34, which also may be referred to as a backplane, and a piezoelectric receiver layer 36. In some implementations, each pixel circuit 32 may include one or more TFT elements and, in some implementations, one or more additional circuit elements such as diodes, capacitors, and the like. Each pixel circuit 32 may be configured to convert an electric charge generated in the piezoelectric receiver layer 36 proximate to the pixel circuit into an electrical signal. Each pixel circuit 32 may include a pixel input electrode 38 that electrically couples the piezoelectric receiver layer 36 to the pixel circuit 32. In the illustrated implementation, a receiver bias electrode 39 is disposed on a side of the piezoelectric receiver layer 36 proximal to platen 40. The receiver bias electrode 39 may be a metallized electrode and may be grounded or biased to control which signals are passed to the TFT array. Ultrasonic energy that is reflected from the exposed (top) surface of the platen 40 is converted into localized electrical charges by the piezoelectric receiver layer 36. These localized charges are collected by the pixel input electrodes 38 and are passed on to the underlying pixel circuits 32. The charges are amplified by the pixel circuits 32 and then provided to the control electronics, which processes the amplified signals. A simplified schematic of an example pixel circuit 32 is shown in FIG. 3A, however one of ordinary skill in the art will appreciate that many variations of and modifications to the example pixel circuit 32 shown in the simplified schematic may be contemplated.

Control electronics 50 may be electrically connected with the first transmitter electrode 24 and the second transmitter electrode 26, as well as with the receiver bias electrode 39 and the pixel circuits 32 on the substrate 34. The control electronics 50 may operate substantially as discussed previously with respect to FIGS. 1A-1C.

The platen 40 can be any appropriate material that can be acoustically coupled to the receiver, with examples including plastic, ceramic and glass. In some implementations, the platen 40 can be a cover plate, e.g., a cover glass or a lens glass for a display. Detection and imaging can be performed through relatively thick platens if desired, e.g., 3 mm and above.

Examples of piezoelectric materials that may be employed according to various implementations include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be employed include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer 22 and the piezoelectric receiver layer 36 may be selected so as to be suitable for generating and receiving ultrasonic waves. In one example, a PVDF piezoelectric transmitter layer 22 is approximately 28 µm thick and a PVDF-TrFE receiver layer 36 is approximately 12 µm thick. Example frequencies of the ultrasonic waves are in the range of 5 MHz to 30 MHz, with wavelengths on the order of a quarter of a millimeter or less.

FIGS. 1A through 1C and 2 show example arrangements of ultrasonic transmitters and receivers in an ultrasonic sensor system, with other arrangements possible. For example, in some implementations, the ultrasonic transmitter 20 may be above the ultrasonic receiver 30, i.e., closer to the object of detection. In some implementations, the ultrasonic sensor system may include an acoustic delay layer. For example, an acoustic delay layer can be incorporated into the ultrasonic sensor system 10 between the ultrasonic transmitter 20 and the ultrasonic receiver 30. An acoustic delay layer can be employed to adjust the ultrasonic pulse timing, and at the same time electrically insulate the ultrasonic receiver 30 from the ultrasonic transmitter 20. The delay layer may have a substantially uniform thickness, with the material used for the delay layer and/or the thickness of the delay layer selected to provide a desired delay in the time for reflected ultrasonic energy to reach the ultrasonic receiver 30. In doing so, the range of time during which an energy pulse that carries information about the object by virtue of having been reflected by the object may be made to arrive at the ultrasonic receiver 30 during a time range when it is unlikely that energy reflected from other parts of the ultrasonic sensor system 10 is arriving at the ultrasonic receiver 30. In some implementations, the TFT substrate 34 and/or the platen 40 may serve as an acoustic delay layer.

FIG. 3A depicts a 4×4 pixel array of pixels for an ultrasonic receiver. Each pixel may, for example, be associated with a local region of piezoelectric sensor material, a peak detection diode and a readout transistor; many or all of these elements may be formed on or in the backplane to form the pixel circuit. In practice, the local region of piezoelectric sensor material of each pixel may transduce received ultrasonic energy into electrical charges. The peak detection diode may register the maximum amount of charge detected by the local region of piezoelectric sensor material. Each row of the pixel array may then be scanned, e.g., through a row select mechanism, a gate driver, or a shift register, and the readout transistor for each column may be triggered to allow the magnitude of the peak charge for each pixel to be read by additional circuitry, e.g., a multiplexer and an A/D converter. The pixel circuit may include one or more TFTs to allow gating, addressing, and resetting of the pixel.

Each pixel circuit 32 may provide information about a small portion of the object detected by the ultrasonic sensor system 10. While, for convenience of illustration, the example shown in FIG. 3A is of a relatively coarse resolution, ultrasonic sensor systems having a resolution on the order of 500 pixels per inch or higher that are configured with a layered structure substantially similar to that shown in FIG. 2 have been demonstrated by the present inventors. The detection area of the ultrasonic sensor system 10 may be selected depending on the intended object of detection. For example, the detection area may range from 5 mm×5 mm for a single finger to 3 inches×3 inches for four fingers. Smaller and larger areas may be used as appropriate for the object.

Figure 3B:
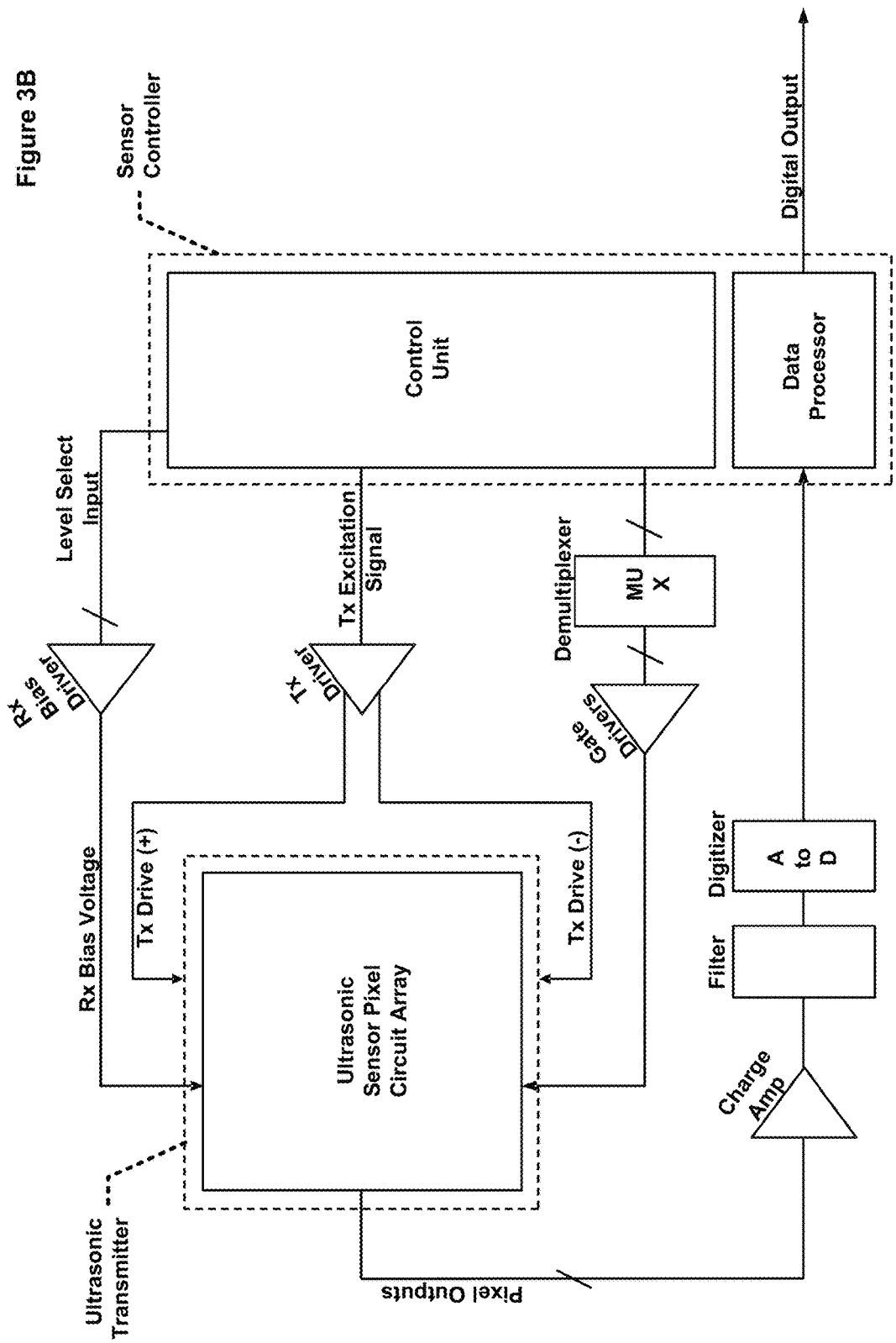
FIG. 3B shows an example of a high-level block diagram of an ultrasonic sensor system.

FIG. 3B shows an example of a high-level block diagram of an ultrasonic sensor system. Many of the elements shown may form part of control electronics 50 (see FIG. 2). A sensor controller may include a control unit that is configured to control various aspects of the sensor system, e.g., ultrasonic transmitter timing and excitation waveforms, bias voltages for the ultrasonic receiver and pixel circuitry, pixel addressing, signal filtering and conversion, readout frame rates, and so forth. The sensor controller may also include a data processor that receives data from the ultrasonic sensor circuit pixel array. The data processor may translate the digitized data into image data of a fingerprint or format the data for further processing. In some embodiments, the digitized data is translated into image data of one or more objects other than a finger or for purposes other than obtaining a fingerprint. For example, an image of a palm, an ear, a face, an inanimate object, or one or more other objects may be obtained and/or processed.

For example, the control unit may send a transmitter (Tx) excitation signal to a Tx driver at regular intervals to cause the Tx driver to excite the ultrasonic transmitter and produce planar ultrasonic waves. The control unit may send level select input signals through a receiver (Rx) bias driver to bias the receiver bias electrode and allow gating of acoustic signal detection by the pixel circuitry. A demultiplexer may be used to turn on and off gate drivers that cause a particular row or column of sensor pixel circuits to provide output signals. Output signals from the pixels may be sent through a charge amplifier, a filter such as an RC filter or an anti-aliasing filter, and a digitizer to the data processor. Note that portions of the system may be included on the TFT backplane and other portions may be included in an associated integrated circuit.

Figure 4:
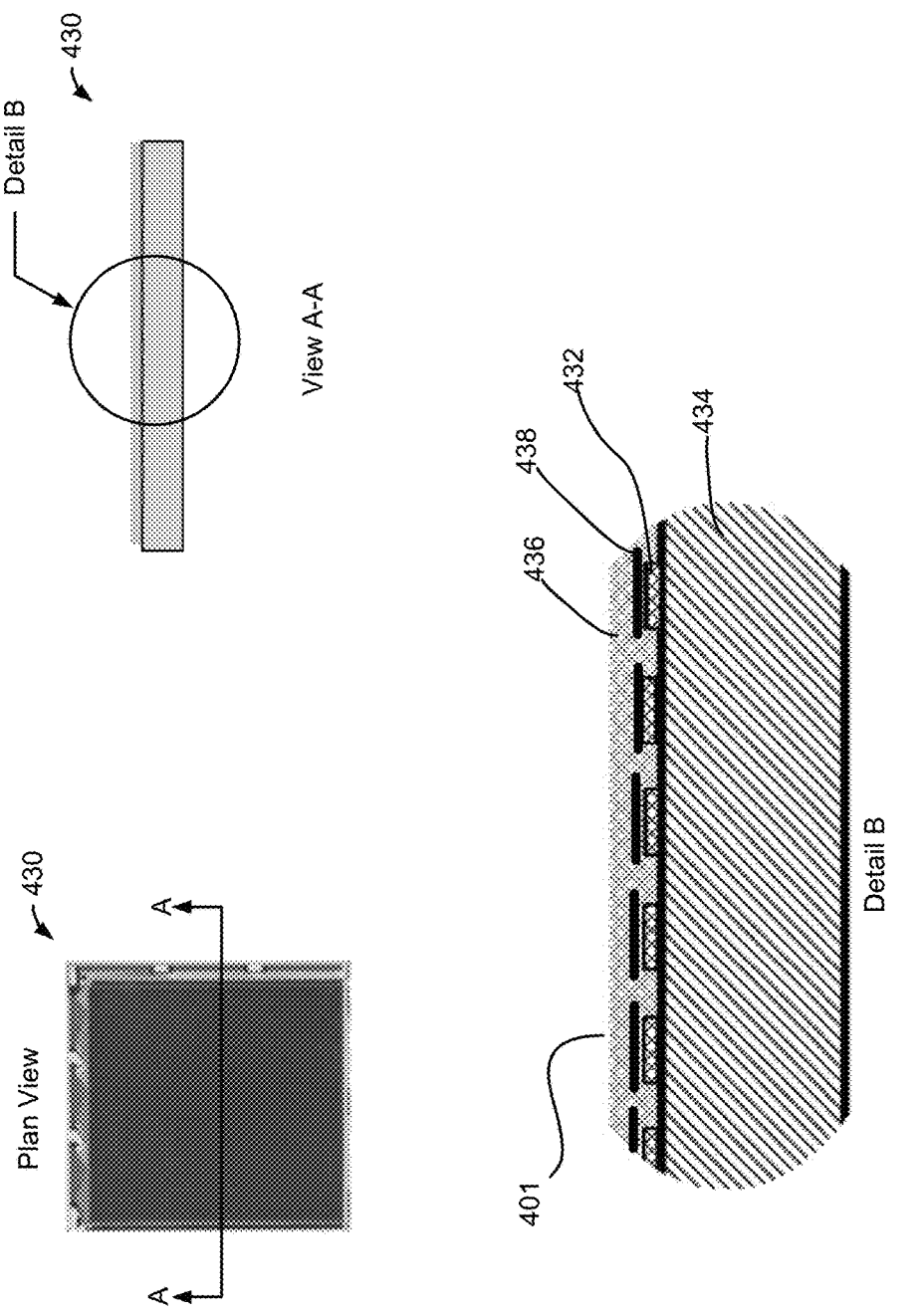
FIG. 4 shows several views of an example of an ultrasonic sensor system according to an implementation.

Some implementations described herein relate to an ultrasonic receiver including a piezoelectric layer. FIG. 4 shows several views of an example of an ultrasonic receiver, according to an implementation. Ultrasonic receiver 430 may be configured to detect ultrasonic energy received at a proximal (input) surface of the receiver. The receiver 430 may include an array of pixel circuits 432 disposed on a substrate 434. In the illustrated implementation, as shown in the "Plan View", the receiver 430 has a rectangular form factor; in other implementations, square or ovoid form factors may be contemplated. In an implementation, the array of pixels may be configured as a 1500×1600 pixel array, and corresponding lateral dimensions of the sensor may be approximately 3.0×3.2 inches.

The array of pixel circuits 432 may be disposed on a top surface of substrate 434. Each pixel circuit 432 may include one or more TFT elements and may include a pixel input electrode 438 in electrical contact with an input to the pixel circuit 432. The pixel input electrode 438 may include a transparent conductive film made, for example, of indium tin oxide (ITO) or indium zinc oxide (IZO).

In an implementation, the ultrasonic receiver 430 may be fabricated by forming a piezoelectric layer 436 over the array of pixel circuits 432 and the top surface of the substrate 434. As will be described in more detail hereinbelow, the piezoelectric layer 436 may be formed by coating a solution containing a copolymer onto the pixel circuits 432, crystallizing the copolymer to form a crystallized copolymer layer, and poling the resulting crystallized copolymer layer to form the piezoelectric layer 436.

It will be appreciated that, for clarity of illustration, certain features of the ultrasonic receiver 430 that would ordinarily be present have been omitted. For example, a receiver bias electrode, such as a conductive layer that is deposited or otherwise affixed onto a top surface 401 of piezoelectric layer 436, as well as details of pixel circuits 432, have been omitted.

Figure 5:
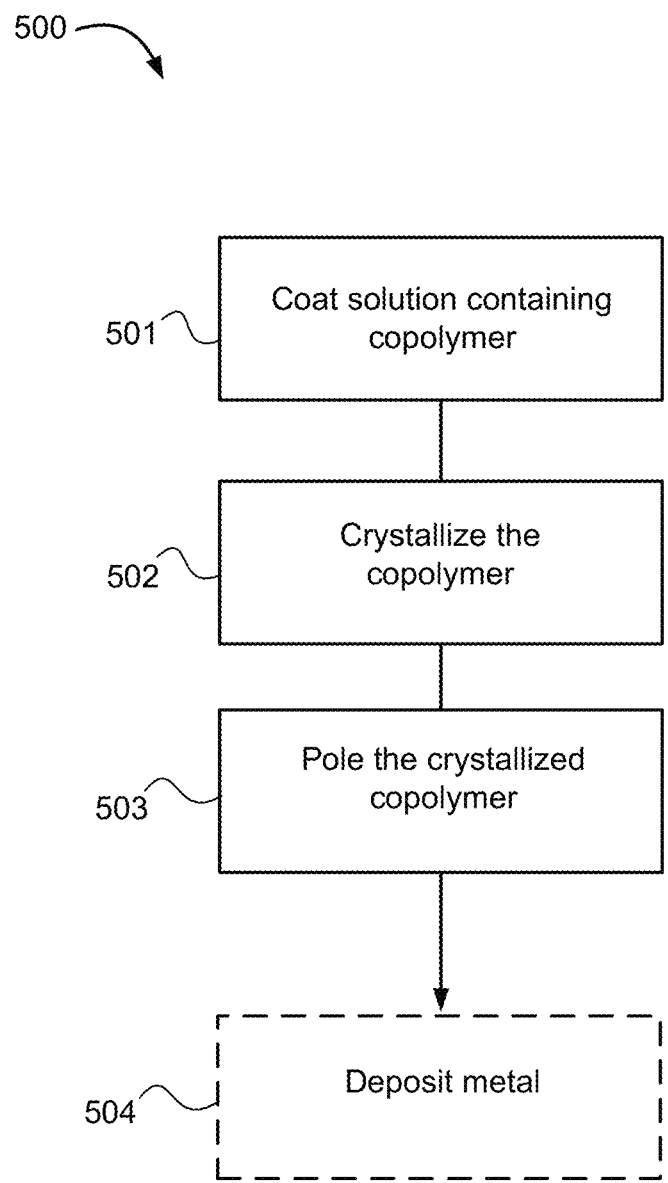
FIG. 5 shows an example of a process flow for fabricating an ultrasonic receiver, according to an implementation.

FIG. 5 shows an example of a process flow for fabricating an ultrasonic receiver, according to an implementation. Process 500 may begin at block 501 with coating a solution containing a copolymer onto an array of pixel circuits, for example pixel circuit array 432. It will be appreciated that the coating may be applied by spin coating, slot coating, dipping, dispensing, spraying, or any other suitable coating process. As described in more detail hereinbelow, a coating process may include or be preceded by application of an adhesion promoter to the array of pixel circuits. Moreover, the coating process may include or be followed by a drying process. In some implementations, the coating process may include coating a solution containing a copolymer onto the TFT backplane.

At block 502, the copolymer may be crystallized. As described in more detail hereinbelow, a crystallization process may include a baking procedure. For example, in some implementations, the pixel circuit array 432 and substrate 438, after being coated with the copolymer, are raised to a temperature above the Curie temperature of the copolymer, but below the melting point of the copolymer. One skilled in the art will appreciate that when a copolymer is held at such a temperature for a sufficient length of time, crystallization of the copolymer will result.

At block 503, the crystallized copolymer may be poled so as to form the piezoelectric layer. As described in more detail hereinbelow, a poling process may include applying a strong electric field across the material so as to align dipoles of the copolymer in a desired orientation. A desired strength of the electric field may vary with the thickness of the crystallized copolymer coating. For example, in some implementations, an electric field strength of approximately 150-200 volts per micron of coating thickness has been found to be effective in forming a piezoelectric layer.

At block 504, optionally, a surface of the piezoelectric layer may be metallized so as to form a receiver bias electrode. As described in more detail hereinbelow, the receiver bias electrode may include a metallized layer such as a first sublayer of copper upon which a second sublayer of nickel is deposited. Alternatively, a layer of silver ink may be disposed on the surface of the piezoelectric layer.

In order to provide a better understanding of certain benefits and features of the presently disclosed techniques, details of some implementations of particular fabrication processes will be described. It will be appreciated that the specific implementations disclosed are examples, and that many possible variations and modifications thereof are within the contemplation of the present disclosure.

Figure 6:
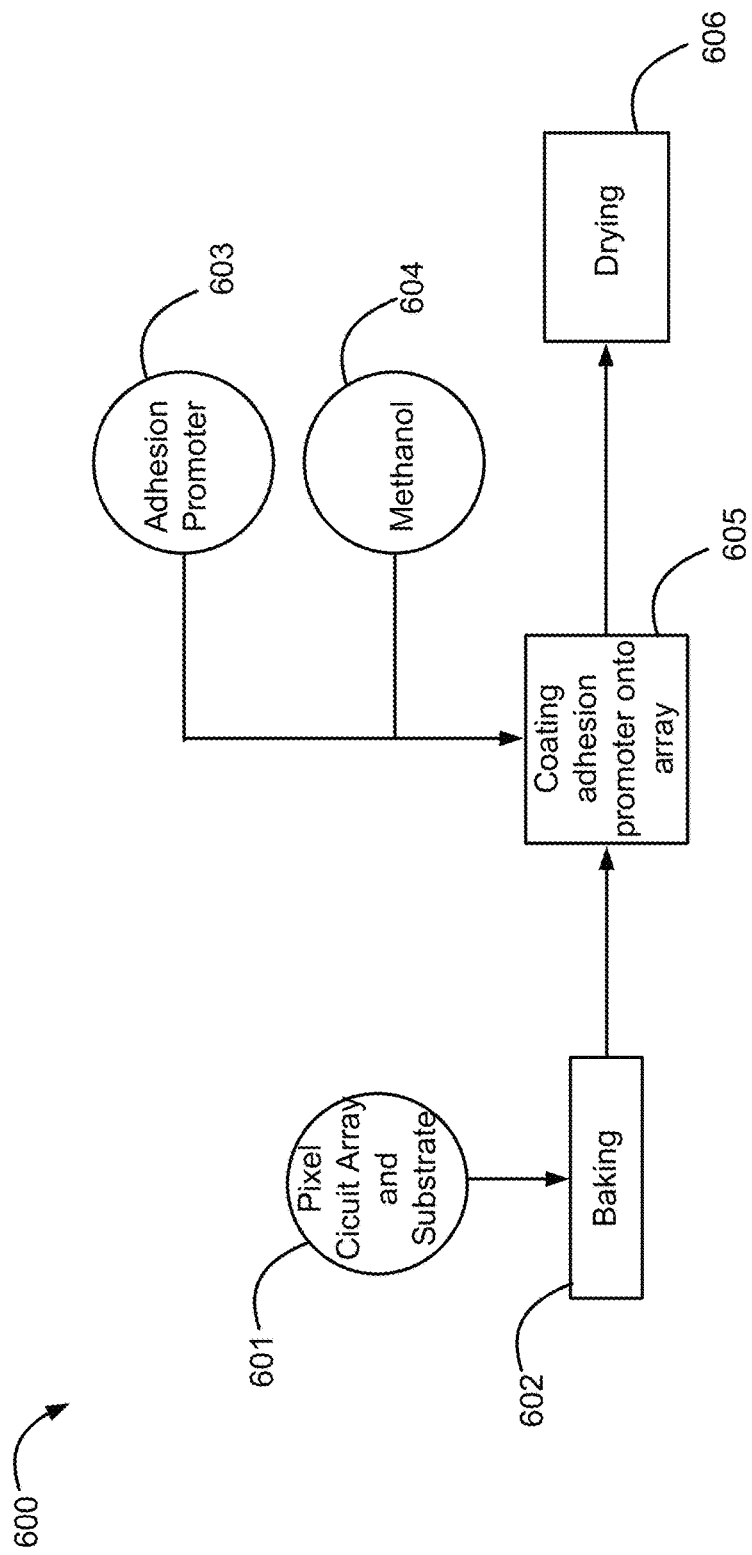
FIG. 6 illustrates an example implementation of an adhesion promoter application process.

FIG. 6 illustrates an example implementation of an adhesion promoter application process that may precede or be included in the process 501 for coating a copolymer onto a pixel circuit array and substrate. Adhesion promoter application process 600 may be advisable taking into account that fluorinated compounds such as many of the copolymers contemplated by the present disclosure have very poor adhesive characteristics. An assembly 601, including a pixel circuit array and a substrate, may enter the process 600 by way of baking operation 602. Baking operation 602 may be performed to help ensure that there are no oils or moisture left from prior processing that may impede good results in coating operation 605. Baking operation 602 may be performed under a partial or substantially total vacuum.

Subsequent to baking operation 602, a coating operation 605 may be performed. Coating operation 605 may result in application of an adhesion promoter 603 to selected surfaces of assembly 601. The adhesion promoter 603, in some implementations, may be a solution of silane or hexamethyldisilazane (HMDS) in methanol 604. For example, a 0.25% solution of HMDS has been found to be effective in increasing a bond strength between surfaces of assembly 601 and the copolymer. The adhesion promoter 603 may be applied by spin coating or other means.

Subsequent to coating operation 605, process 600 may continue with a drying operation 606 to evaporate the methanol 604 and otherwise prepare assembly 601 for subsequent processes. In some implementations, water is a curing agent for the adhesion promoter, and the drying operation may be performed in a humid environment, for example at a relative humidity above 60%.

Figure 7:
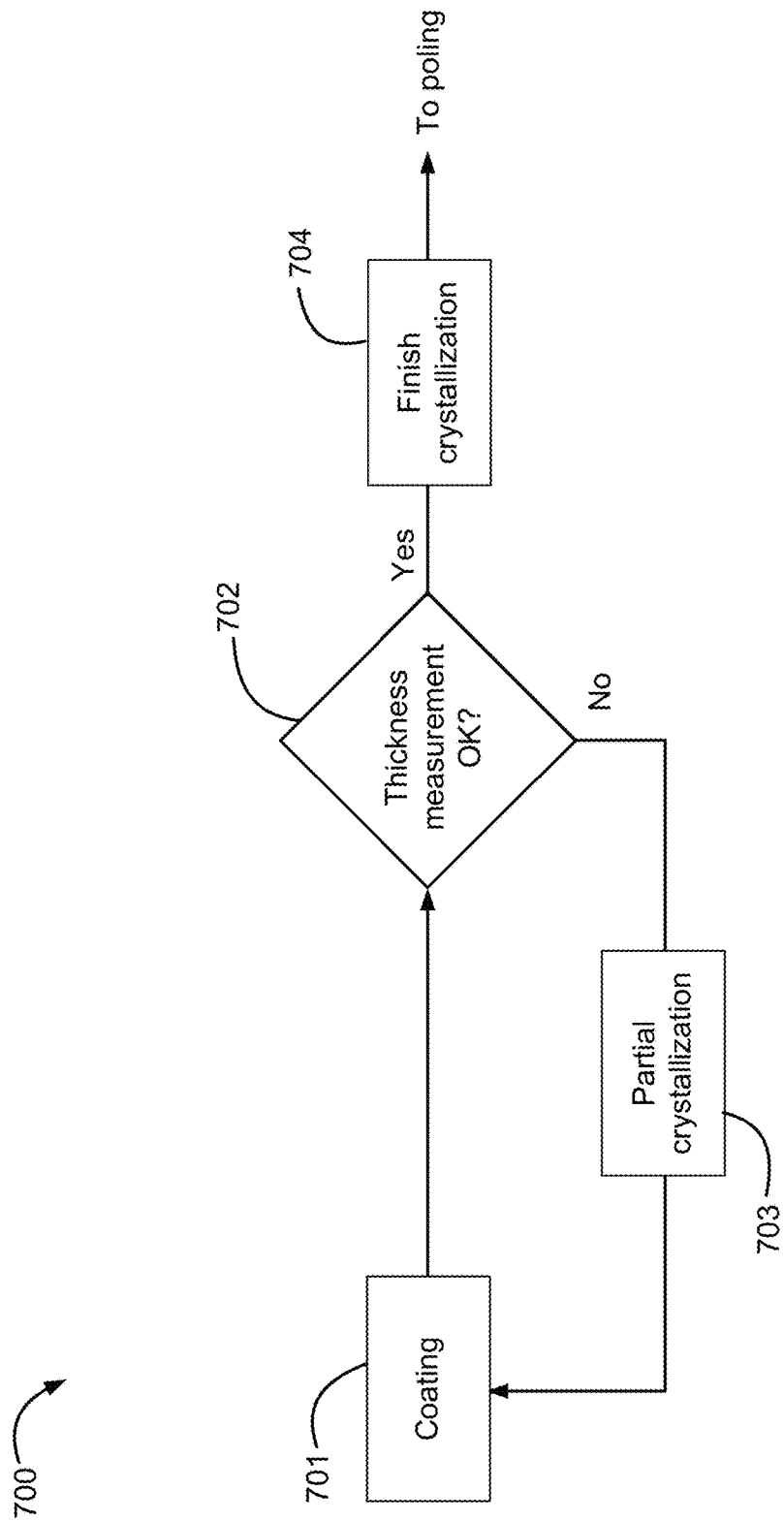
FIG. 7 illustrates an example implementation of a coating and crystallization process.

FIG. 7 illustrates an example implementation of a coating and crystallization process. Process 700 may be performed in connection with or instead of coating process 501 and crystallization process 502, for example. During coating operation 701, a copolymer layer is applied to assembly 601. The copolymer may include PVDF-TrFE at a molar percent ratio of about 80-20, 70-30 or 90-10.

Following coating operation 701, a measurement of the thickness of the copolymer coating may be performed. For example, a thickness of a sublayer deposited by coating operation 701 may be 3-4 μm for example, whereas a total coating thickness of about 10-12 μm may be desired. Accordingly, crystallization process 700 contemplates that a determination made at decision block 702 will result in repeating coating operation 701 one or more times. Between depositing each sublayer, a partial crystallization operation 703 may be performed. The partial crystallization operation 703 may include raising the temperature of assembly 601 to a temperature above the Curie temperature of the copolymer, but below the melting point of the copolymer. In some implementations, the Curie temperature of the copolymer may be 135° C. and the melting point may be 150° C. In an example process, therefore, assembly 601 may be held at a temperature of 135° C. for a period of time sufficient to achieve partial, but not complete, crystallization. Desirably, the partial crystallization causes a preceding sublayer deposited by coating operation 701 to be relatively insoluble during a subsequent coating operation 701. It will be appreciated that a sufficient period of time for partial crystallization will depend, inter alia, on the composition of the copolymer. In some implementations, for a molar percent ratio of 70-30, for example, thirty minutes has been found to be sufficient, whereas for a molar percent ratio of 80-20, one hour may be preferable.

When a determination is made at decision block 702 that the desired total coating thickness has been obtained, process 700 may proceed to block 704 and finish crystallization of the copolymer by raising the temperature of assembly 601 to a temperature above the Curie temperature of the copolymer, but below the melting point of the copolymer for a period of time sufficient to allow crystallization to reach a point at which the copolymer is capable of becoming a piezoelectric material. Operation 704 may complete the transformation of the copolymer from an amorphous material to a crystalline material that was initiated at block 703. Details of operation 704 may depend upon the exact copolymer used (molar ratio of PVDF to TrFE, for example). For the 70-30 copolymer, 135 C for 3 hours has been found to be effective, whereas for the 80-20 copolymer 135 C for 12 hours has been found to be effective.

In an implementation, operation 704 results in achieving a crystallization state such that the average crystal size is greater than a dipole domain length and less than a size that will not be able to orient in an electric field. It will be appreciated that the optimum time and temperature conditions may be determined in a laboratory using, for example, differential scanning calorimetry to plot phase changes versus time for a constantly increasing (or decreasing) temperature.

Figure 8:
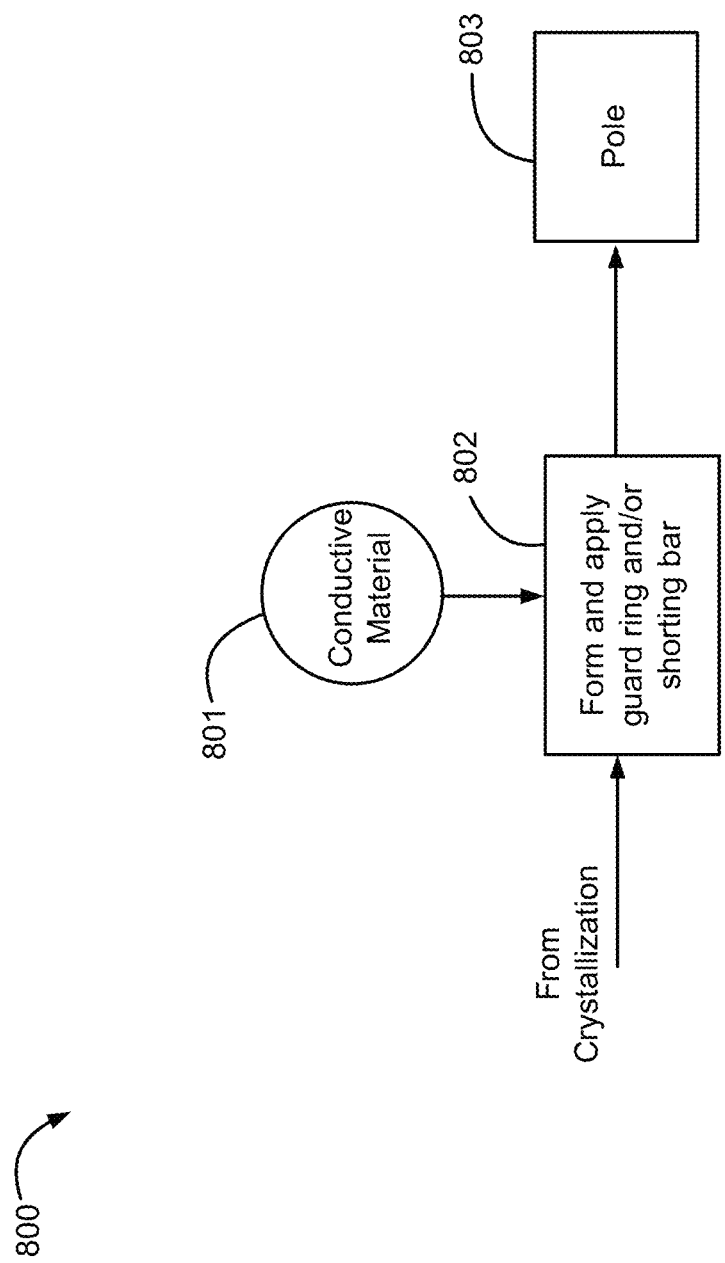
FIG. 8 illustrates an example implementation of a poling process.

FIG. 8 illustrates an example implementation of a poling process 800 that may be applied to the copolymer so as to form a piezoelectric layer. Process 800 may be performed in connection with or instead of process 503, for example. As noted above, a poling process may include applying a strong electric field across the material so as to align dipoles of the copolymer in a desired orientation. To protect the array of pixel circuits that may include a number of voltage-sensitive components including TFTs, poling process 800 may include precautions that protect the voltage-sensitive components. For example, a conductive material 801 may be applied to electrically short input and output terminals of the pixel circuits to ground. Conductive material 801 may be a conductive rubber or silver ink compound, for example. In some implementations, the conductive material may be approximately coplanar with and extend circumferentially around pixel circuit array 432. For example, at block 802, a guard ring and/or a shorting bar of conductive rubber or silver ink may be provided.

At block 803, a poling operation is executed. In some implementations, a field strength of approximately 150-200 volts per micron of coating thickness is applied in a dry partial vacuum with an array of needles and a copper grid.

Subsequent to poling, the guard ring and/or shorting bar may be removed. For example, the silver ink compound may be removed by application of a reagent such as isopropyl alcohol or other reagent in which the silver ink is soluble. In some embodiments utilizing a guard ring, the guard ring is removed during a dicing process, for example by cutting the ring off when cutting the TFT glass.

Figure 9:
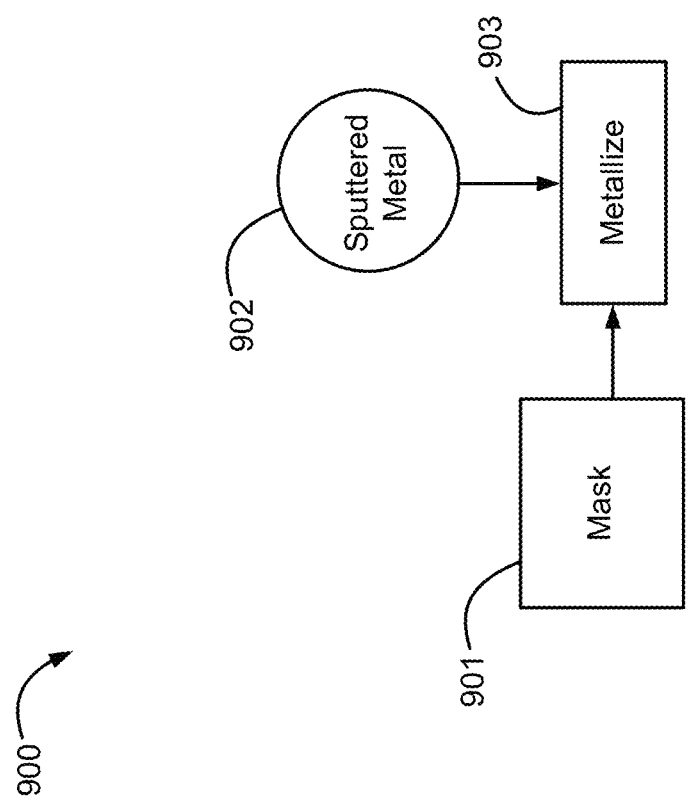
FIG. 9 illustrates an example implementation of a metallization process.

FIG. 9 illustrates an example implementation of a metallization process 900 that may be applied to the piezoelectric layer so as to form the receiver bias electrode. Process 900 may be performed in connection with or instead of process 504, for example. At block 901, a masking operation may be executed to prevent metallization from occurring in undesired areas. For example, an active area of the piezoelectric layer may be metallized at block 903 by depositing a sputtered metal 902 through a shadow mask, which occludes portions of the pixel circuit array and/or the substrate to avoid depositing metal on the occluded portions. The resulting receiver bias electrode may include a first sublayer of copper, upon which a second sublayer of nickel is deposited. In some implementations, the copper sublayer may have a thickness of about 150 Å whereas the nickel sublayer may have a thickness of about 850 Å. In other implementations one or more sublayers of copper/nickel, aluminum, titanium, chromium/nickel, chromium/molybdenum, and gold have been combined in various thicknesses.

One or more operations of the fabrication methods described in this disclosure can be implemented in apparatus including one or more stations or modules for placing one or more components, bonding two or more components together, preparing and applying coatings, and/or dispensing conductive inks or epoxies, and a controller including program instructions for conducting the fabrication methods. In some implementations, a controller may include one or more memory devices and one or more processors configured to execute the program instructions so that the apparatus can perform a method in accordance with the disclosed implementations. The processor may include a central processing unit (CPU) or a computer, analog and/or digital input/output connections, motor controller boards, and other like components. Program instructions for implementing appropriate process operations may be executed on or by the processor. These program instructions may be stored on the memory devices or other machine-readable media associated with the controller or they may be provided over a network.

In some implementations, the controller may control all, most, or a subset of the operations of an apparatus. For example, the controller may control all or most the operations of an associated with dispensing of a conductive ink or laminating an adhesive. The controller may execute system control software including sets of instructions for controlling the timing of the process operations, pressure levels, temperature levels and other parameters of particular manufacturing processes further described with respect to FIGS. 5 through 9. In some implementations, other computer programs, scripts, or routines stored on memory devices associated with the controller may be employed.

In some implementations, a user interface may be associated with the controller. The user interface may include a display screen, graphical software to display process conditions, and user input devices such as pointing devices, keyboards, touch screens, microphones, and other like components.

In some implementations, the program instructions for controlling the operations of an apparatus may include computer program code written in any conventional computer readable programming language, such as, for example, assembly language, C, C++, Pascal, FORTRAN, or others. Compiled object code or script may be executed by the processor of the controller to perform the tasks identified in the program instructions.

In some implementations, signals for monitoring a manufacturing process may be provided by analog and/or digital input connections of the controller. Signals for controlling a manufacturing process may be output on analog and/or digital output connections of the controller.

The various illustrative logics, logical blocks, modules, circuits and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some implementations, particular steps and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, apparatus.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blue-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Thus, an ultrasonic receiver having an array of pixel circuits coated with a polymeric piezoelectric layer has been disclosed. While various embodiments have been described herein, it should be understood that they have been presented by way of example only, and not limitation. It will thus be appreciated that those skilled in the art will be able to devise numerous systems and methods which, although not explicitly shown or described herein, embody said principles of the invention and are thus within the spirit and scope of the invention as defined by the following claims.

As used herein, a phrase referring to "at least one of" a list of items refers to any combination of those items, including single members. As an example, "at least one of: a, b, or c" is intended to cover: a, b, c, a-b, a-c, b-c, and a-b-c.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of a component as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, a person having ordinary skill in the art will readily recognize that such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A method for fabricating an ultrasonic receiver configured to detect ultrasonic energy received at a first surface of the ultrasonic receiver, the ultrasonic receiver including an array of pixel circuits disposed on a substrate, the method comprising:
    coating a solution containing a polymer onto a first side of the array of pixel circuits, each pixel circuit in the array including at least one thin film transistor (TFT) element and a pixel input electrode;
    subsequent to coating the solution, crystallizing the polymer to form a crystallized polymer layer; and
    executing a poling process that includes applying an electric field across the crystallized polymer layer to form a piezoelectric layer that is in electrical contact with the pixel input electrodes.

2. The method of claim 1, wherein the pixel input electrode is formed from a conductive film.

3. The method of claim 1, wherein coating the solution containing the polymer onto the first side of the array of pixel circuits includes coating an adhesion promoter onto the array of pixel circuits.

4. The method of claim 1, wherein coating the solution containing the polymer is performed by spin coating, slot coating, dipping, dispensing, spraying, or another coating process.

5. The method of claim 1, wherein the polymer includes a ferroelectric polymer.

6. The method of claim 1, wherein the polymer has a characteristic Curie temperature and a melting point, and crystallizing the polymer includes baking the polymer at a temperature between the Curie temperature and the melting point for at least one hour.

7. The method of claim 1, wherein a conductive material is applied to electrically short terminals of the pixel circuits to ground prior to the poling.

8. The method of claim 7, wherein the conductive material is a conductive rubber or a conductive ink.

9. The method of claim 1, further including a receiver bias electrode deposited on the piezoelectric layer.

10. The method of claim 9, wherein the receiver bias electrode includes a first sublayer of copper and a second sublayer of nickel.

11. The method of claim 10, wherein the first sublayer is about 150 angstroms thick and the second sublayer of nickel is about 850 angstroms thick.

12. The method of claim 1, wherein poling includes applying an electric field with a field strength between 150 and 200 volts per micron through the polymer layer.

* * * * *